(12) United States Patent
Gandhi

(10) Patent No.: US 9,192,460 B2
(45) Date of Patent: Nov. 24, 2015

(54) HOLLOW FIBER URETERAL STENT AND FILTER

(71) Applicant: Cook Medical Technologies LLC, Bloomington, IN (US)

(72) Inventor: Neena Gandhi, Bloomington, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 0 days.

(21) Appl. No.: 14/136,965

(22) Filed: Dec. 20, 2013

(65) Prior Publication Data

US 2014/0188247 A1  Jul. 3, 2014

Related U.S. Application Data

(60) Provisional application No. 61/746,883, filed on Dec. 28, 2012.

(51) Int. Cl.
*A61F 2/04* (2013.01)
*A61M 27/00* (2006.01)
*A61F 2/00* (2006.01)

(52) U.S. Cl.
CPC ............... *A61F 2/04* (2013.01); *A61M 27/008* (2013.01); *A61F 2002/009* (2013.01); *A61F 2002/048* (2013.01); *A61F 2210/009* (2013.01); *A61F 2220/0008* (2013.01)

(58) Field of Classification Search
CPC .................... A61F 2002/048; A61F 2002/047; A61M 25/00; A61M 37/00; A61M 27/008
USPC .................... 604/8; 623/23.65, 23.66, 23.7
See application file for complete search history.

(56) References Cited

U.S. PATENT DOCUMENTS

| | | |
|---|---|---|
| 3,767,759 A | 10/1973 | Wichterle et al. |
| 4,432,853 A | 2/1984 | Banks |
| 4,960,415 A | 10/1990 | Reinmuller |
| 5,722,931 A | 3/1998 | Heaven |
| 6,096,019 A | 8/2000 | Andrews |
| 6,395,021 B1 | 5/2002 | Hart et al. |
| 6,491,720 B1 | 12/2002 | Vallana et al. |
| 6,605,068 B2 | 8/2003 | Righetti |
| 6,945,950 B2 | 9/2005 | Clayman et al. |
| 7,182,758 B2 | 2/2007 | McCraw |
| 7,763,142 B2 | 7/2010 | Watson |
| 7,874,998 B2 | 1/2011 | Humes et al. |
| 8,109,894 B2 | 2/2012 | Noda et al. |
| 8,133,344 B2 | 3/2012 | Ishibashi et al. |

(Continued)

FOREIGN PATENT DOCUMENTS

WO  88/05317  7/1988

OTHER PUBLICATIONS

European Search Report, EP 13198355, report completed Feb. 28, 2014, 8pp.

*Primary Examiner* — Thomas J Sweet
*Assistant Examiner* — Wade P Schutte
(74) *Attorney, Agent, or Firm* — Brinks Gilson & Lione

(57) ABSTRACT

An endoluminal prosthesis for placing in a body passage of a patient, includes a ureteral stent, the ureteral stent comprising a generally tubular housing having a proximal end and a distal end and a lumen longitudinally disposed therethrough, at least one hollow fiber tubule disposed within the tubular housing, and at least one anchoring mechanism disposed on a distal end of the tubular housing.

20 Claims, 6 Drawing Sheets

(56) References Cited

U.S. PATENT DOCUMENTS

| | | | |
|---|---|---|---|
| 2003/0120261 A1* | 6/2003 | Gellman | 604/544 |
| 2005/0165342 A1 | 7/2005 | Odland | |
| 2007/0060834 A1* | 3/2007 | Odland et al. | 600/561 |
| 2009/0105811 A1 | 4/2009 | Dinh et al. | |
| 2010/0076481 A1 | 3/2010 | Stephens et al. | |
| 2010/0100061 A1 | 4/2010 | Odland | |

* cited by examiner

HOLLOW FIBER URETERAL STENT AND FILTER

RELATED APPLICATIONS

The present application claims priority to U.S. Provisional Patent Application Ser. No. 61/746,883 filed Dec. 28, 2012, the entirety of which is hereby incorporated by reference.

TECHNICAL FIELD

The invention relates generally to medical devices and, particularly, medical devices useful for urinary drainage.

BACKGROUND

Minimally-invasive surgery has evolved to a point where procedures that were unimaginable a few years ago are now routinely performed on a daily basis. Indwelling ureteral stents have been widely used for years. Such stents are placed in the ureter, which is the duct between the kidney and the bladder, for the purpose of establishing and/or maintaining an open, patent flow of urine from the kidney to the bladder.

Nephrolithiasis is a condition in which one or more calculi or stones are present in the kidneys. Kidney stones affect 3-5% of the world population and 80% of the stones are calcium-based; calcium oxalate being predominant. Other stones are made up of calcium phosphate, uric acid, cystine or struvite (magnesium ammonium phosphate). Small crystal aggregates are typically excreted from the body via passage in urine. Once the aggregates grow to a certain size (3 mm) however, they can cause obstruction of the ureters due to urolithiasis.

Ureteral stents may be used to retain patency of the ureteral lumen and to continue normal urinary drainage following the treatment and removal of stones and calculi from kidneys and ureters. To treat this condition, several individual steps are involved. In one procedure, these steps include placing a relatively narrow wire guide through a urethra and a bladder, and then through the ureter and into the kidney. After the wire guide is placed, a catheter is run along the wire guide, dilating the body passage (the urethra and the ureter) as it moves down the wire guide. The access sheath also dilates the body passages as it moves from outside the body, through the urethra, and into the ureter, down the desired location, and into or very near the kidney.

The physician may then remove calculi and stones through the access sheath, using a grasper, a retrieval basket or other device. The access sheath protects the ureter from repeated passage of the retrieval device while the stones or calculi are removed. After the stones are removed, the ureteral stent may be placed into the ureter through the access sheath, using the catheter or a pushing tube to position the stent.

Lifetime risk of nephrolithiasis in the developed world is 10-15%, and is higher elsewhere (20-25% in the Middle East). In the US, nephrolithiasis is estimated to occur in up to 10% and 5% of the male and female population respectively, result in medical costs of $2.1 billion annually. 70% of those who experience nephrolithiasis will have recurrence of stones even after surgical removal. Once recurrent, the subsequent risk of relapse is raised and the interval between recurrences is shortened. Crystallization of calcium and magnesium salts is the chief culprit in the formation of kidney stones.

The typical ureteral stent can be composed of various radiopaque polymers, including polyethylene, silicone, polyurethane, and thermoplastic elastomers. These stents are retained in the ureter by a retentive anchoring portion, such as a curved shape, pigtail, coil, J-shape, or hook configuration, at either end of the stent that engages the walls of the bladder and the kidney, respectively. The stent is resilient to allow it to be straightened for insertion into a body passageway and returned to its predetermined retentive anchoring shape when in situ. There can be problems, however, with ureteral stents, as urine may fail to drain through the stent. This may be due to a number of reasons, such as extrinsic compression of the stent or blockage of the drainage mechanism of the stent by encrustation. Furthermore, there can be problems associated with migration of the ureteral stent from the original implantation site either upward into the kidney of the patient or downward into the bladder of the patient.

BRIEF SUMMARY

In one aspect, an endoluminal prosthesis for placing in a body passage of a patient, includes a ureteral stent, the ureteral stent comprising a generally tubular housing having a proximal end and a distal end and a lumen longitudinally disposed therethrough, at least one hollow fiber tubule disposed within the tubular housing, the at least one hollow fiber tubule comprising an external membrane, and internal membrane, and a lumen therethrough; and at least one anchoring mechanism disposed on a distal end of the generally tubular housing. The at least one hollow fiber tubule is configured to filter bacteria and salt crystals from urine. In some embodiments, the hollow fiber tubule includes an external membrane layer, an inner membrane layer, and a lumen. In other embodiments, the external membrane of the hollow fiber tubules is microporous or nanoporous.

In another aspect, an endoluminal prosthesis for placing in a body passage of a patient includes a ureteral stent having a proximal and a distal end and a lumen longitudinally disposed therethrough, the ureteral stent including a hollow fiber tubule having an external membrane and an internal membrane and at least one anchoring mechanism disposed on the ureteral stent. In some embodiments, the external membrane layer and the internal membrane layer are negatively charged. The hollow fiber tubule is configured to filter bacteria and salt crystals from urine. In other embodiments, a pharmaceutically active carrier is disposed on outer surface of the hollow fiber tubule.

In yet another aspect, a kit for placing an endoluminal prosthesis includes a ureteral stent, the ureteral stent having a generally tubular housing having a proximal end and a distal end and a lumen longitudinally disposed therethrough, at least one hollow fiber tubule disposed within the tubular housing, and at least one anchoring mechanism disposed on the generally tubular housing; an introduction assembly, the introduction assembly having a wire shaft having a proximal end and a distal end and a first magnet connected to the distal end of the wire shaft; and an access sheath surrounding the ureteral stent and the introduction assembly, where the first magnet is configured to engage with a corresponding magnet on at least one anchoring mechanism. In some embodiments, the at least one anchoring member comprises a malecot.

In still another aspect, method for implanting an endoluminal prosthesis into a body, including providing a ureteral stent, the ureteral stent having a generally tubular housing having a proximal end and a distal end and a lumen longitudinally disposed therethrough, at least one hollow fiber tubule disposed within the tubular housing, and at least one anchoring mechanism disposed on the tubular housing; engaging the ureteral stent with an introduction assembly, the introduction assembly comprising a wire shaft having a proximal end and a distal end and a first magnet connected to the distal end of the wire shaft; placing a wire guide along a body path to a location desired for the prosthesis, inserting an access sheath along the wire guide and advancing the access sheath to the desired position; removing the wire guide; advancing the ureteral stent within the access sheath to the desired location using a stent positioner; and at least partially removing the access sheath and deploying the ureteral stent by disengaging the ureteral stent from the introduction assembly.

DETAILED DESCRIPTION OF THE DRAWINGS AND THE PRESENTLY PREFERRED EMBODIMENTS

Figure 1A:
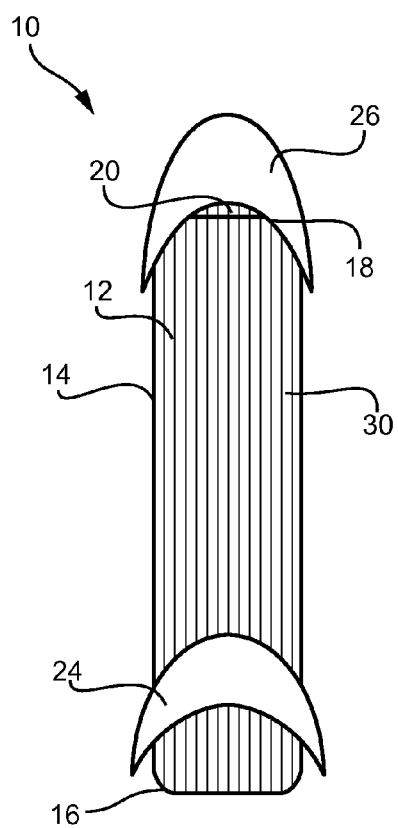
FIGS. 1a-1c depicts an embodiment of an endoluminal prosthesis having a hollow fiber tubule.

Unless otherwise defined, all technical and scientific terms used herein have the same meaning as commonly understood by one of ordinary skill in the art to which this invention pertains. In case of conflict, the present document, including definitions, will control. Preferred methods and materials are described below, although methods and materials similar or equivalent to those described herein can be used in the practice or testing of the present invention. The materials, methods, and examples disclosed herein are illustrative only and not intended to be limiting.

The terms "comprise(s)," "include(s)," "having," "has," "can," "contain(s)," and variants thereof, as used herein, are intended to be open-ended transitional phrases, terms, or words that do not preclude the possibility of additional acts or structures. The present invention also contemplates other embodiments "comprising," "consisting of and "consisting essentially of," the embodiments or elements presented herein, whether explicitly set forth or not.

The terms "about" or "substantially" used with reference to a quantity includes variations in the recited quantity that are equivalent to the quantity recited, such as an amount that is insubstantially different from a recited quantity for an intended purpose or function.

The term "prosthesis" means any device for insertion or implantation into, or replacement, for a body part or function of that body part. It may also mean a device that enhances or adds functionality to a physiological system. The term prosthesis may include, for example and without limitation, a stent, stent-graft, filter, valve, balloon, embolization coil, and the like.

The term "endoluminal" refers to or describes the internal or inside of a lumen, duct, and other passageways or cavities located in a human or other animal body. A lumen or a body passageway may be an existing lumen or a lumen created by surgical intervention. As used in this specification, the terms "lumen" or "body passageway," and "vessel" are intended to have a broad meaning and encompass any duct (e.g., natural or iatrogenic) or cavity within the human body and may include, without limitation, blood vessels, respiratory ducts, gastrointestinal ducts, such as the biliary duct, intestines, the esophagus, the pericardial cavity, the thoracic cavity, and the like. Accordingly, the terms "endoluminal device" or "endoluminal prosthesis" describe devices that can be placed inside or moved through any such lumen or duct.

The terms "patient," "subject," and "recipient" as used in this application may refer to any animal, particularly humans.

The terms "proximal" and "distal" will be used to describe opposing axial ends of the ureteral stent, as well as the axial ends of various component features. The term "proximal" is used to refer to the end of the ureteral stent (or component thereof) that is closest to the operator during use of the system. The term "distal" is used to refer to the end of the ureteral stent (or component thereof) that is initially inserted into the patient, or that is closest to the patient during use.

The term "biocompatible" refers to a material that is substantially non-toxic in the in vivo environment of its intended use, and that is not substantially rejected by the patient's physiological system (i.e., is non-antigenic). This can be gauged by the ability of a material to pass the biocompatibility tests set forth in International Standards Organization (ISO) Standard No. 10993 and/or the U.S. Pharmacopeia (USP) 23 and/or the U.S. Food and Drug Administration (FDA) blue book memorandum No. G95-1, entitled "Use of International Standard ISO-10993, Biological Evaluation of Medical Devices Part-1: Evaluation and Testing." Typically, these tests measure a material's toxicity, infectivity, pyrogenicity, irritation potential, reactivity, hemolytic activity, carcinogenicity and/or immunogenicity. A biocompatible structure or material, when introduced into a majority of patients, will not cause a significantly adverse, long-lived or escalating biological reaction or response, and is distinguished from a mild, transient inflammation which typically accompanies surgery or implantation of foreign objects into a living organism.

The term "medical device" means any object that is itself or that includes a component that is intentionally inserted into the body of a patient as part of a medical treatment, and that comprises a structure adapted for introduction into a patient. The medical device can be a tool, such as, without limitation, a catheter, a wire guide, a forceps, or a scissors used to affect a surgical procedure at and/or deliver a second medical device to a treatment site in a patient. An alternative medical device of the present invention is one that is commonly intended to be a permanent implant, such as a stent.

The term "implantable" refers to the ability of a medical device to be positioned, partially or wholly, at a location within a body of a human or veterinary patient for any suitable period of time, such as within a vessel. Implantable medical devices can include devices configured for bioabsorption within a body during prolonged period of time.

The term "controlled release" refers to the release of a material, such as a pharmacologically active ingredient, at a predetermined rate. A controlled release may be characterized by a drug elution profile, which shows the measured rate that the material is removed from a material-containing device in a given solvent environment as a function of time. A controlled release does not preclude an initial burst release associated with the deployment of the medical device. The release may be a gradient release in which the concentration of the material released varies over time or a steady state release in which the material is released in equal amounts over a certain period of time (with or without an initial burst release).

The term "pharmacologically active ingredient" refers to any agent that produces an intended therapeutic effect on the body to treat or prevent conditions or diseases.

A more detailed description of the embodiments will now be given with reference to FIGS. 1a-9. The present invention is not limited to those embodiments illustrated; it specifically contemplates other embodiments not illustrated but intended to be included in the claims.

Figure 1B:
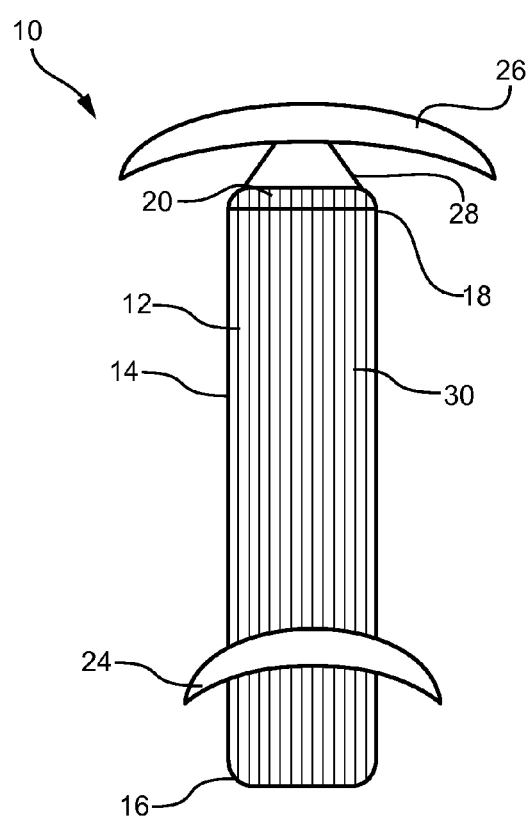
Figure 1C:
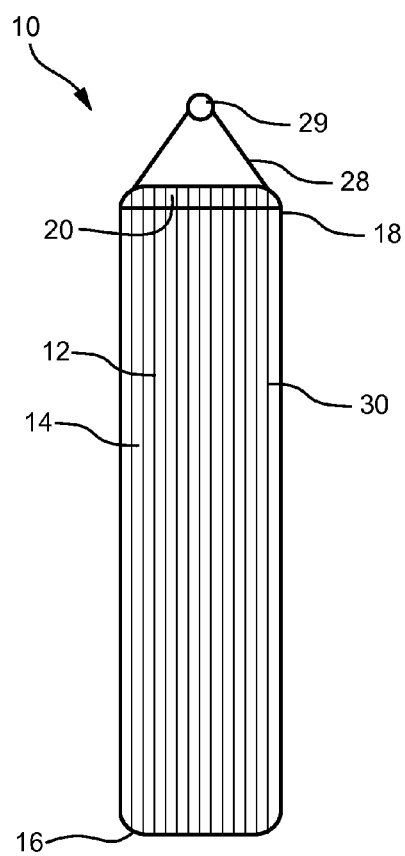

FIGS. 1a-1c show an embodiment of an endoluminal prosthesis 10. As shown, the prosthesis 10 comprises a ureteral stent 12 having an elongated housing 14. The elongated housing 14 of the ureteral stent 12 has a generally tubular configuration. The ureteral stent 12 further includes a proximal end 16 and a distal end 18 and a lumen 20 disposed therethrough. Disposed within the lumen 20 of the ureteral stent 12 is a plurality of semi permeable hollow fiber tubules 30. The ureteral stent 12 may have a length of about 12 cm to about 32 cm and preferably having outer diameters in the range of about 4 Fr to about 10 Fr. The ureteral stent 12 may be manufactured from any suitable biocompatible material, including, but not limited to, polyester-based biocompatible polymers, nylon-based polymers, polytetrafluoroethylene (PTFE) polymers, silicone polymers, polyurethane polymers, polyethylene polymers, and thermoplastic polymers. The ureteral stent 12 may be comprised of bio-resorbable materials including, but not limited to, chitosan, chitin, and polylactic acid. The ureteral stent 12 further includes a proximal anchoring mechanism 24 attached to the proximal end 16 of the elongated housing 14 and a distal anchoring mechanism 26. As shown in FIG. 1b, the distal end 18 of the ureteral stent 12 includes a hollow, non-porous cap 28 to which the proximal anchoring mechanism may be attached. FIG. 1c shows the distal end of the ureteral stent 12 in greater detail. In FIG. 1c, the distal anchoring mechanism 26 has been removed to reveal features of the ureteral stent 12 that may be covered by the distal mechanism 26. A magnet 29 may be attached to the cap 28. As will be discussed below, the magnet 29 may interact with a corresponding magnet on an introduction assembly used to deliver the ureteral stent 12.

Referring back to FIGS. 1a and 1b, the proximal anchoring mechanism 24 and the distal anchoring mechanism 26 in this embodiment each comprise a retention sleeve having a generally hemispherical configuration. The distal anchoring mechanism 26 is configured to be positioned in a distal portion of the ureter, preferably in close proximity to the ureteropelvic junction. The proximal anchoring mechanism 24 is configured to be positioned in a proximal portion of the ureter, preferably in close proximity to the ureterovesical junction. The position of the proximal anchoring mechanism 24 and the distal anchoring mechanism 26 allows the ureteral stent 12 to be retained within the ureter without coming into contact with the bladder or the kidney of the patient. As shown, the distal anchoring mechanism 24 is sized to be slightly larger than the proximal anchoring mechanism 24. One of ordinary skill in the art would understand that the size of the proximal anchoring mechanism 24 and the distal anchoring mechanism 26 may be altered depending on patient needs. The proximal anchoring mechanism 24 and the distal anchoring mechanism 26 each have a collapsed configuration and an open configuration. In the collapsed configuration, as shown in FIG. 1a, the proximal anchoring mechanism 24 and the distal anchoring mechanism 26 are in close contact with the outer surface of the ureteral stent 12. In this configuration, the width of each anchoring mechanism 24, 26 does not exceed the diameter of the ureteral stent 12 by more than 1 Fr. In the open configuration, as shown in FIG. 1b, the proximal anchoring mechanism 24 and the distal anchoring mechanism 26 expand radially into the generally hemispherical configuration. In this configuration, the width of each anchoring mechanism 24, 26 does not exceed the diameter of the ureteral stent 12 by about 2 Fr. to about 3 Fr.

Figure 2:
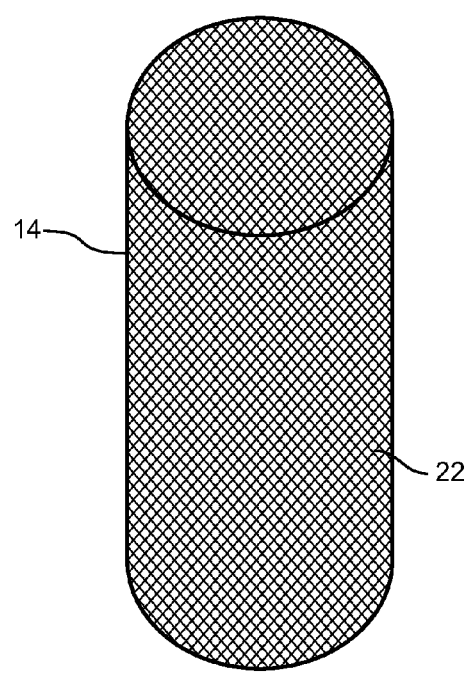
FIG. 2 depicts an embodiment of an elongate housing of the ureteral stent of FIG. 1.

FIG. 2 shows an embodiment of the elongate housing 14 in greater detail. As shown, the elongated housing 14 includes a plurality of pores 22 forming a mesh. The pores 22 are configured to allow urine to enter into the interior surface of the hollow body such that they provide no barriers to flow or transport of urine. The size of the pores 22 may range from about 1 $cm^2$ to 5 $cm^2$. In the present embodiments, the pores 22 are disposed throughout the entire length of the elongated body. In alternative embodiments, the pores 22 may only be disposed in a portion of the elongated body.

Figure 3A:
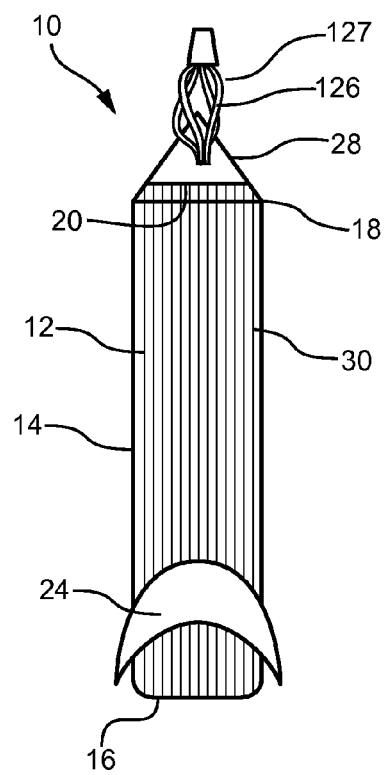
FIGS. 3a-3c depict alternative embodiments of distal retention members for use with the ureteral of FIG. 1.
Figure 3B:
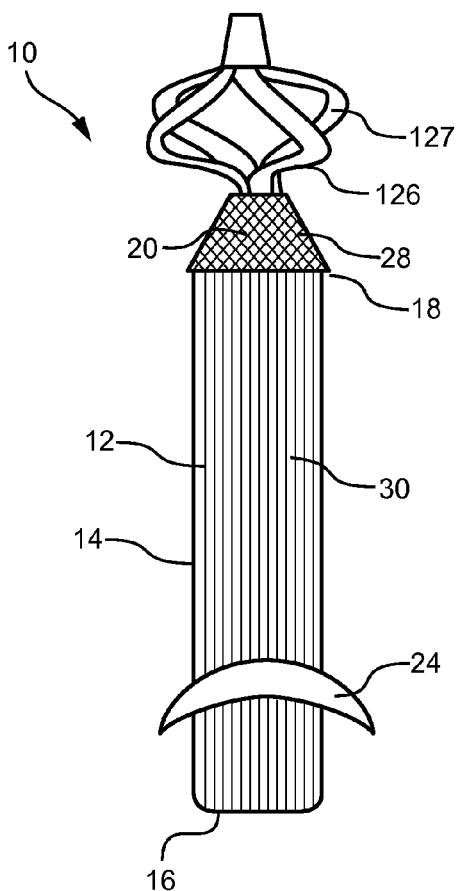
Figure 3C:
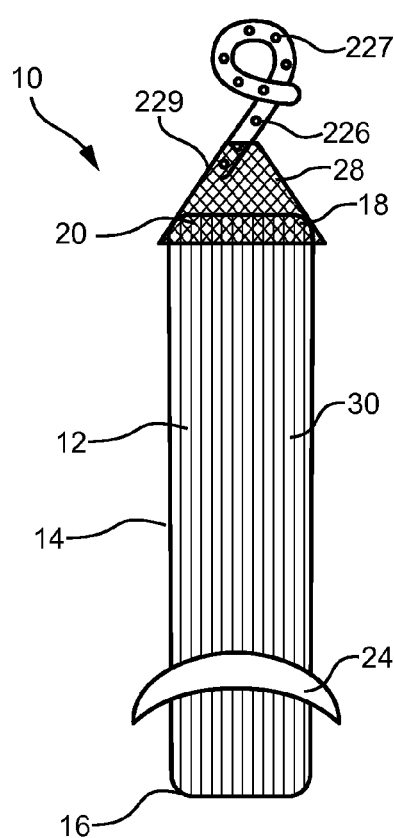

FIGS. 3a-3c show alternative embodiments of a distal anchoring mechanism 26 on the ureteral stent 12. FIGS. 3a and 3b shows a distal retention 26 having a generally malecot configuration having an outlet. The distal anchoring mechanism 126 in this embodiment has a collapsed configuration and an open configuration. When the distal anchoring mechanism 126 is in the collapsed configuration, as shown in FIG. 3a, the wires 127 of the distal anchoring mechanism 126 are disposed in close proximity with a longitudinal axis of the ureteral stent 12. When the distal anchoring mechanism is in the open configuration, as shown in FIG. 3b, the wires 127 of the malecot expand radially about the distal end 18 of the ureteral stent 12. FIG. 3c shows a distal anchoring mechanism 226 having a generally pigtail shape having a plurality of openings 227. The distal anchoring mechanism 226 includes an outlet 229 on its proximal end that is in fluid communication with the lumen 20 of the ureteral stent 12.

Figure 4:
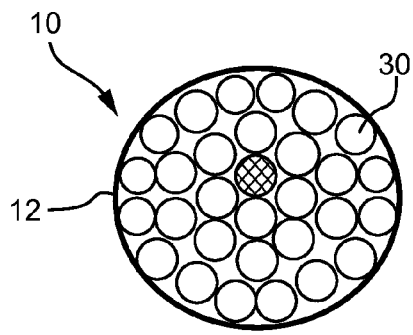
FIG. 4 depicts a cross sectional view of the ureteral stent of FIG. 1.

FIG. 4 shows a cross-section view of the ureteral stent 12. As shown, the hollow fiber tubules 30 are positioned within the lumen 20 of the ureteral stent 12 in a single, dense bundle in a parallel configuration. The dense packaging of the hollow fiber tubules 30 helps prevent lateral movement of the hollow fiber tubules 30 within the lumen 20 of the ureteral stent 12. Each hollow fiber tubule 30 may have a diameter of about 200 nm. The hollow fiber tubules 30 may be comprised of biocompatible materials. Examples of suitable biocompatible materials include, but are not limited to, polysulfone, polyethersulfone, polyethylene, polyvinyl chloride, polyvinylidene fluoride mixed cellulose ester polyether-segmented nylon, polyurethane, and silicone. The hollow fiber tubules may also be manufactured from bio-resorbable materials. One of ordinary skill in the art would understand that suitable materials may have differences in their porosity, molecular weight, and hydrophilicity. In a preferred embodiment, the prosthesis may comprise polysulfones, which can be obtained in non-cytotoxic and bioconformity versions.

Figure 5:
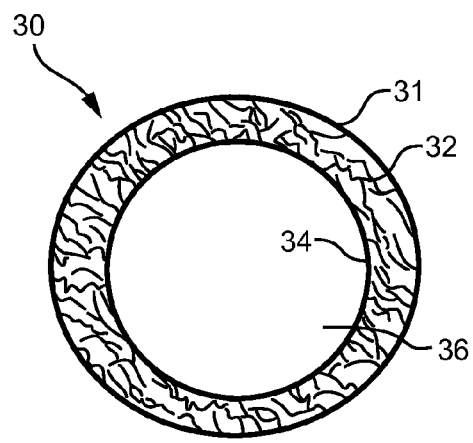
FIG. 5 depicts a cross sectional view of a hollow fiber tubule of the ureteral stent of FIG. 1.

FIG. 5 shows the hollow fiber tubule 30 in closer detail. The hollow fiber tubules 30 comprise an outer surface 31, an external membrane 32, an internal membrane 34, and a lumen 36. The external membrane 32 may be microporous or nanoporous, while the internal membrane 34 is generally macroporous. The larger pores of the internal membrane 34 and the smaller pores of the external membrane 32 create a concentration gradient favorable to the diffusion of small molecules across each membrane of the hollow fiber tubule 30. When the ureteral stent 12 is placed within the ureter, urine passing through the ureter and the lumen of the ureteral stent will first come into contact with the external membrane of the hollow fiber tubes. The microporous or nanoporous external membrane will allow small molecules within the urine, such as water, to pass through the membrane while larger molecules, such as salt crystals and bacteria are prevented from passing through the membrane. Once the larger molecules within the urine have been filtered from smaller molecules, the small molecules pass through the macroporous internal membrane layer 34 with minimal resistance, and into the lumen 36 of the hollow fiber tubule 30. The filtered urine then exits the lumen 36 of the hollow fiber tubule 30 into the bladder. This filtering reduces the amount of microorganisms as well as the mineral salt deposits in the urine, which subsequently reduces the probability of the ureteral stent 12 becoming blocked due to encrustation and/or infection to the patient. Continuous urine flow outside the tubules helps to reduce fouling the external surface of the hollow fiber tubules 30 and housing 14 due to the buildup of salt.

One of ordinary skill in the art would understand how to prepare and manufacture the hollow fiber tubules 30 by suitable means. Exemplary means of preparation are presented in Jaap van't Hof, "Wet Spinning of asymmetric hollow fibre membranes for gas separation in many suitable ways," (1988) (unpublished Thesis, University of Twente), available at http://doc.utwente.nl/75400/1/1988_Hof_van_'t.pdf, which discloses two routes—melt spinning and wet spinning. In the melt spinning process, a polymer is heated in the range of 200° C.-400° C. for a short duration in an inert atmosphere and then extruded into fibers. Immediate air cooling will result in a homogeneous fiber wall. In the wet spinning process, a polymer is dissolved in a solvent and extruded into a film developed on a support or spun into fiber sing a spinneret. The film is then exposed to air and subsequent nonsolvent bath, where precipitation of the polymer occurs. The use of a second nonsolvent in the bore of the fiber results in fixation from the inside. The end-result is asymmetric hollow fibers. The formation of the internal membrane is further encouraged by maintenance of an airgap between the spinneret and nonsolvent bath, allowing evaporation of the solvent. Parameters in the membrane formation process, such as core liquid pressure, membrane-forming mixture pressure, air gap size, relative humidity in air gap and stable temperature, may be configured to obtain the desired thickness and porosities of the skin and bulk layers.

Embodiments of the ureteral stent 12 may include additional functionalities introduced during manufacturing. One exemplary embodiment may include charged membranes. In this embodiment, the active groups at the membrane surface level may be modified to express the desired surface charge. The charged membranes may be positively charged or negatively charged. In some negatively charged membranes, carboxyl, acetate, and/or sulfonyl groups of the chosen material bind cations, such as calcium and magnesium, which typically precipitate out of urine and form insoluble salts that result in encrustation.

One or more pharmacologically active agents, such as medications or drugs, may be placed on the surface of the hollow fiber tubules 30 in order to assist in patient care and comfort. For instance, an antimicrobial drug may help to reduce inflammation and microbial activity in the vicinity of the stent. Analgesics, such as aspirin or other non-steroidal anti-inflammatory drugs, may also be applied to the surface of the hollow fiber tubules to reduce pain and swelling upon implantation of the stent. Chemotherapeutic drugs like mitomycin or immunotherapeutics such as interferons may be applied to the surface of the hollow fiber tubules 30 and gradually released in urothelial cancer treatment. Bactericidal, fungicidal or bacteriostatic drugs may be used to reduce microbial colonization and/or biofilm formation. Other medications, such as alpha-blockers, may also be used. Alpha-blockers are drugs that block receptors in arteries and smooth muscles. In the urinary tract, alpha-blockers relax the walls of the tract and enhance urinary flow. Examples of suitable alpha-blockers include, but are not limited to, doxazosin, alfuzosin, tamsulosin, prazosin, and terazosin.

Any of these pharmacologically active agents is preferably applied in a controlled release so that the beneficial effect of the drug is sustained over a period of at least several weeks or months. This may be especially helpful in the case where the stent will remain in place for a considerable length of time.

Embodiments of the ureteral stent 12 comprising pharmacologically active elements may be used for prophylactic applications as well as therapeutic applications. The drug of interest may be covalently bound to the surface of the hollow fiber tubule so that the drug remains active at the surface. In other embodiments, the drug may be bound to the hollow fiber tubule 30 through other suitable means including electrostatic or adsorptive forces, which allows the drug to elute over the course of the indwelling period of the prosthesis, permitting a gradual and continual release of high local drug concentrations. Suitable particular applications for a drug eluting prosthesis may include modulation of urine components or pH, taking advantage of the specific and non-specific binding of various chemicals to different polymers.

Figure 6:
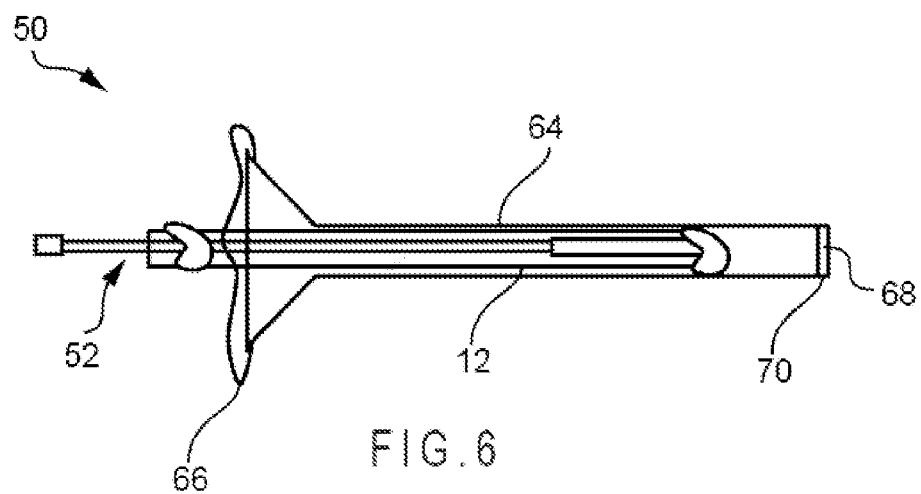
FIG. 6 depicts a kit for delivering the ureteral stent of FIG. 1.

FIG. 6 depicts an embodiment of a kit 50 for delivering the ureteral stent 12. As shown, the kit 50 comprises an introduction assembly 52, a ureteral access sheath 64, and the ureteral stent 12. The access sheath 64 includes a proximal end 66 and a distal end 68. An opening 70 is provided on the distal end 68 of the access sheath 64. The access sheath may be made from any suitable biocompatible material, for example polytetrafluoroethylene (PTFE), nylon, or polyethylene. As shown, the introduction assembly 52 and the access sheath 66 help to maintain the ureteral stent 12 in an undeployed position and each anchoring mechanism 24, 26 in the collapsed configuration.

Figure 7:
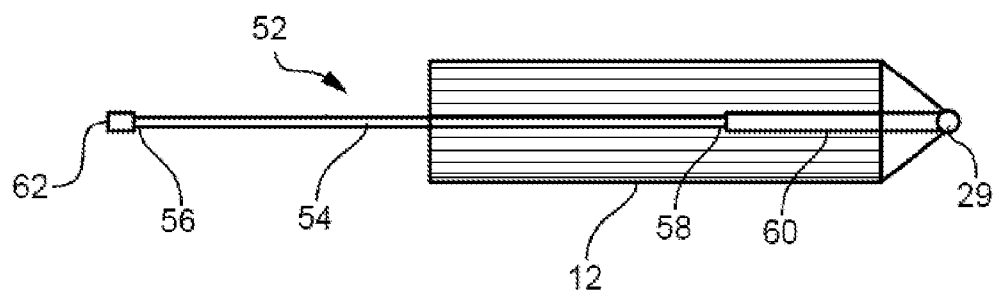
FIG. 7 depicts an embodiment of an introduction assembly for use with the ureteral stent of FIG. 1.

FIG. 7 shows an embodiment of the introduction assembly 52 in greater detail. The introduction assembly 52 comprises a wire shaft 54 having a proximal portion 56 and a distal portion 58. A first magnet 60 is disposed on the distal portion 58 of the introduction assembly 52. The first magnet 60 is configured to removeably engage with the corresponding magnet 29 on the distal end of the ureteral stent 12. The proximal portion 56 of the introduction assembly 52 is configured to remain outside of the patient. A second magnet 62 may be attached to the proximal end of the introduction assembly 52. The second magnet 62 would be configured to have a stronger magnetic pull force than the first magnet 60. The second magnet 62 may be used to remove the introduction assembly 52 following deployment of the ureteral stent 12 in the ureter.

In use, a physician places a wire guide through a urethra, bladder, and a ureter into a kidney. After the wire guide is placed, the access sheath 64 is guided along the wire guide. The distal opening 70 of the access sheath 64 is generally positioned at or near the ureteropelvic junction of the patient. Once the access sheath 64 is in position, the wire guide is removed. The ureteral stent 12, held in an undeployed position by the introduction assembly 52, is inserted into the access sheath 64 and advanced through the inner lumen of the access sheath 64. A stent positioner may be used to advance the prosthesis through the access sheath. The ureteral stent 12 is advanced through the access sheath 64 until the distal end 18 of the ureteral stent 12 exits the distal opening 70 of the access sheath 64. Once the ureteral stent 12 is in the correct position near the ureteropelvic junction, the introduction assembly 52 is rotated and each retention assembly 24, 26 expands into the open configuration. The position of the stent positioner is maintained by the physician while withdrawing the access sheath 64. This continual withdrawal of the access sheath 64 allows the ureteral stent 12 to expand and deploy within the ureter. Following the deployment of the ureteral stent 12, the physician can remove the stent positioner and the access sheath 64 from the patient. The introduction assembly 52 may be removed by applying the second magnet 62 to the proximal portion 56 of the wire shaft 52 and moving the second magnet 62 in the proximal direction. One of ordinary skill in the art would understand that the introduction assembly 52 may be removed by other suitable means.

Figure 8:
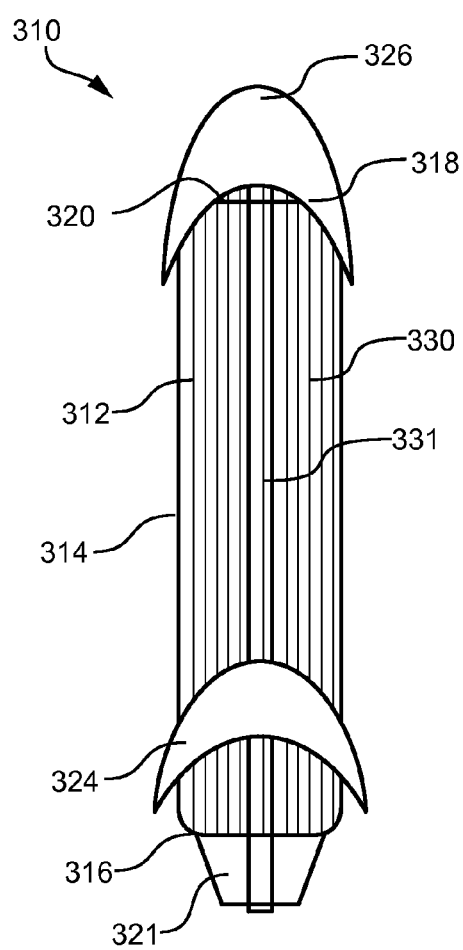
FIG. 8 depicts an alternative embodiment of an endoluminal prosthesis having a hollow fiber tubule.

FIG. 8 shows an alternative embodiment of an endoluminal prosthesis 310. As shown, the prosthesis 310 comprises a ureteral stent 312 having an elongated housing 314. The elongated housing 314 of the ureteral stent 312 has a generally tubular configuration. The ureteral stent 312 further includes a proximal end 316, a distal end 318, and a lumen 320 disposed therethrough. The ureteral stent 312 further has a proximal anchoring mechanism 324 attached to the proximal end 316 of the elongated housing 314 and a distal anchoring mechanism 326. In this embodiment, the proximal anchoring mechanism 324 and the distal anchoring mechanism 326 each comprise a retention sleeve having a generally hemispherical configuration. Disposed within the lumen 318 of the elongate body is a plurality of semi permeable hollow fiber tubules 330. The ureteral stent 312 further includes an outlet 321 positioned at its proximal end 316. As shown, the outlet 321 has a generally conical shape. In alternative embodiments, the outlet may have a different configuration including, but not limited to, spherical or cylindrical. The outlet 321 is entirely hollow and is configured to channel the urine flowing through the lumen of the hollow fiber tubules to exit the ureteral stent 312 and enter the bladder of the patient. An inner tube 323 may be positioned in the lumen 320 of the ureteral stent 312. The inner tube 323 is configured to provide a guided entry way for an introduction assembly. In this embodiment, the inner tube 323 includes a magnet on its distal end. The magnet will be configured to engage with a corresponding magnet on the introduction assembly.

Figure 9:
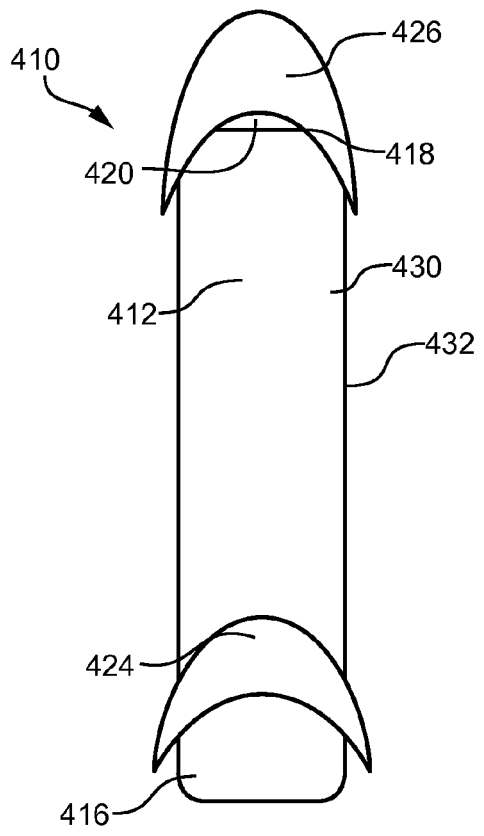
FIG. 9 depicts an alternative embodiment of an endoluminal device having a hollow fiber tubule.

FIG. 9 shows an alternative embodiment of a endoluminal prosthesis 410. As shown, the prosthesis 410 comprises a ureteral stent 412 having an generally tubular configuration. The ureteral stent 412 further includes a proximal end 416 and a distal end 418. The ureteral stent 412 further has a proximal anchoring mechanism 424 attached to the proximal end 416 of the ureteral stent 412 and a distal anchoring mechanism 426. In this embodiment, the proximal anchoring mechanism 424 and the distal anchoring mechanism 426 each comprise a retention sleeve having a generally hemispherical configuration. The ureteral stent 412 is comprised of a single hollow fiber tubule 430. The hollow fiber tubule 430 comprises an external membrane 432, an internal membrane (not shown) and a lumen 420 disposed therethrough. The ureteral stent 412 may have a length of about 12 cm to about 32 cm and preferably having outer diameters in the range of about 4 Fr to about 10 Fr. The hollow fiber tubule 430 of the ureteral stent 412 may be comprised of biocompatible materials including, but not limited to, polysulfone, polyethersulfone, polyethylene, polyvinyl chloride, polyvinylidene fluoride mixed cellulose ester polyether-segmented nylon, polyurethane, and silicone. The hollow fiber tubule may also be manufactured from bio-resorbable materials.

A method for implanting an endoluminal prosthesis into a body, comprising, providing a ureteral stent, the ureteral stent comprising a generally tubular housing having a proximal end and a distal end and a lumen longitudinally disposed therethrough, at least one hollow fiber tubule disposed within the tubular housing, and and at least one anchoring mechanism disposed on the tubular housing; engaging the ureteral stent with an introduction assembly, the introduction assembly comprising a wire shaft having a proximal end and a distal end and a first magnet connected to the distal end of the wire shaft; placing a wire guide along a body path to a location desired for the prosthesis, inserting an access sheath along the wire guide and advancing the access sheath to the desired position; removing the wire guide; advancing the ureteral stent within the access sheath to the desired location using a stent positioner; and at least partially removing the access sheath and deploying the ureteral stent by disengaging the ureteral stent from the introduction assembly.

Throughout this specification various indications have been given as to preferred and alternative embodiments of the invention. However, the foregoing detailed description is to be regarded as illustrative rather than limiting and the invention is not limited to any one of the provided embodiments. It will be evident to one skilled in the art that modifications and variations may be made without departing from the spirit and scope of the invention. Changes in form and in the proportion of parts, as well as the substitution of equivalents, are contemplated as circumstances may suggest and render expedience; although specific terms have been employed, they are intended in a generic descriptive sense only and not for the purpose of limiting the scope of the invention set forth in the following claims. Moreover, the device is not limited to any specific dimension or material discussed above, nor is the device limited to being used with saline or an image contrast fluid alone.

The invention claimed is:

1. An endoluminal prosthesis for placing in a body passage of a patient comprising
    a ureteral stent, the ureteral stent comprising a generally tubular housing having a proximal end and a distal end and a lumen longitudinally disposed therethrough,
    at least one hollow fiber tubule disposed within the tubular housing, the at least one hollow fiber tubule comprising an external membrane layer, and internal membrane layer, and a lumen; and
    at least one anchoring mechanism disposed on the tubular housing,
    wherein the at least one hollow fiber tubule is configured to filter bacteria and salt crystals from urine.

2. The endoluminal prosthesis of claim 1, wherein the generally tubular housing is porous.

3. The endoluminal prosthesis of claim 2, wherein the pores of the generally tubular housing range from about 1 cm$^2$ to 5 cm$^2$.

4. The endoluminal prosthesis of claim 1, wherein the external membrane layer is microporous or nanoporous.

5. The endoluminal prosthesis of claim 1, wherein the internal membrane layer is macroporous.

6. The endoluminal prosthesis of claim 1, wherein the external membrane layer and the internal membrane layer are negatively charged.

7. The endoluminal prosthesis of claim 1, wherein a pharmaceutically active carrier is disposed on outer surface of the at least one hollow fiber tubule.

8. The endoluminal prosthesis of claim 1, wherein a pharmaceutically active carrier is disposed on an outer surface and an inner surface of the generally tubular housing.

9. The endoluminal prosthesis of claim 1, wherein the at least one anchoring member comprises a generally hemispherical sleeve.

10. The endoluminal prosthesis of claim 1, wherein the at least one anchoring member further includes a magnet, the magnet configured to engage with a corresponding magnet of an introduction assembly.

11. The endoluminal prosthesis of claim 1, further comprising an outlet disposed proximal of the at least one hollow fiber tubule.

12. The endoluminal prosthesis of claim 1, further comprising an inner tube disposed through the lumen of the tubular housing.

13. An endoluminal prosthesis for placing in a body passage of a patient comprising,
- a ureteral stent having a proximal end and a distal end and a lumen longitudinally disposed therethrough, the ureteral stent comprising at least one hollow fiber having an external membrane and an internal membrane; and
- at least one anchoring mechanism disposed on the ureteral stent,
- wherein the hollow fiber tubule is configured to filter bacteria and salt crystals from urine.

14. The endoluminal prosthesis of claim 13, wherein the external membrane layer is microporous or nanoporous and the internal membrane layer is macroporous.

15. The endoluminal prosthesis of claim 13, wherein the external membrane layer and the internal membrane layer are negatively charged.

16. The endoluminal prosthesis of claim 13, wherein the at least one anchoring member comprises a generally hemispherical sleeve.

17. The endoluminal prosthesis of claim 13, wherein the at least one anchoring member further includes a magnet.

18. The endoluminal prosthesis of claim 13, wherein a pharmaceutically active carrier is disposed on outer surface of the hollow fiber tubule.

19. The endoluminal prosthesis of claim 13, further comprising an inner tube disposed through the lumen of the tubular housing.

20. A kit for placing an endoluminal prosthesis comprising,
- a ureteral stent, the ureteral stent comprising
  - a generally tubular housing having a proximal end and a distal end and a lumen longitudinally disposed therethrough,
  - at least one hollow fiber tubule disposed within the tubular housing, and
  - at least one anchoring mechanism disposed on the tubular housing;
- an introduction assembly, the introduction assembly comprising a wire shaft having a proximal end and a distal end and a first magnet connected to the distal end of the wire shaft; and
- an access sheath surrounding the ureteral stent and the introduction assembly;
- where the first magnet is configured to engage with a corresponding magnet on at least one anchoring mechanism.

\* \* \* \* \*